United States Patent
Yabushita

(10) Patent No.: US 11,448,589 B2
(45) Date of Patent: Sep. 20, 2022

(54) ANALYZER, ANALYSIS METHOD, AND A PROGRAM RECORDING MEDIUM RECORDED WITH A PROGRAM FOR ANALYZER

(71) Applicant: HORIBA, LTD., Kyoto (JP)

(72) Inventor: Hirotaka Yabushita, Kyoto (JP)

(73) Assignee: HORIBA, LTD., Kyoto (JP)

( * ) Notice: Subject to any disclaimer, the term of this patent is extended or adjusted under 35 U.S.C. 154(b) by 89 days.

(21) Appl. No.: 16/912,050

(22) Filed: Jun. 25, 2020

(65) Prior Publication Data

US 2020/0408675 A1 Dec. 31, 2020

(30) Foreign Application Priority Data

Jun. 25, 2019 (JP) .............................. JP2019-117758

(51) Int. Cl.
*G01N 21/35* (2014.01)
*G01N 21/3504* (2014.01)
*G01N 33/00* (2006.01)

(52) U.S. Cl.
CPC ..... *G01N 21/3504* (2013.01); *G01N 33/0004* (2013.01); *G01N 2021/3509* (2013.01); *G01N 2021/3595* (2013.01)

(58) Field of Classification Search
CPC ........... G01N 21/3504; G01N 33/0004; G01N 2021/3509; G01N 2021/3595
See application file for complete search history.

(56) References Cited

U.S. PATENT DOCUMENTS

| 2003/0069703 | A1 | 4/2003 | Rendahl et al. | |
|---|---|---|---|---|
| 2010/0264315 | A1* | 10/2010 | Okada | G01N 21/3504 250/340 |
| 2018/0017540 | A1* | 1/2018 | Miao | G01N 21/3563 |

FOREIGN PATENT DOCUMENTS

| JP | 2009-115654 A | 5/2009 |
|---|---|---|
| WO | 2019031331 A1 | 2/2019 |

OTHER PUBLICATIONS

Notice of Allowance dated Oct. 5, 2021 issued in JP patent application No. 2019-117758, 5 pgs.

\* cited by examiner

*Primary Examiner* — Hugh Maupin
(74) *Attorney, Agent, or Firm* — Brooks Kushman P.C.

(57) ABSTRACT

An analyzer analyzes a measurement sample on the basis of spectrum data obtained by irradiating light to the measurement sample. The analyzer includes a main analysis part, a correlation data storage part and a concentration calculation part. The main analysis part calculates a concentration of a predetermined hydrocarbon component contained in the measurement sample on the basis of the spectrum data of the measurement sample. The correlation data storage part stores therein a plurality of correlation data each indicating a correlation between a concentration of the predetermined hydrocarbon component or the spectrum data and a THC concentration. The concentration calculation part selects at least one correlation data from among a plurality of correlation data stored in the correlation data storage part according to the concentration of the predetermined hydrocarbon component, and calculates a concentration of the total hydrocarbon components in the measurement sample by using correlation data thus selected.

12 Claims, 4 Drawing Sheets

ANALYZER, ANALYSIS METHOD, AND A PROGRAM RECORDING MEDIUM RECORDED WITH A PROGRAM FOR ANALYZER

CROSS-REFERENCE TO RELATED APPLICATION

This application claims priority to Japanese Application No. 2019-117758, filed Jun. 25, 2019, the disclosure of which is incorporated in its entirety by reference herein.

BACKGROUND OF THE INVENTION

Field of the Invention

The present invention relates to an analyzer to analyze a measurement sample on the basis of spectrum data obtained by irradiating light to the measurement sample.

Background Art

An FID analyzer and a spectroscopic analyzer, such as an FTIR, have conventionally been used for measuring a concentration and an amount of a total hydrocarbon (THC) contained in, for example, automotive exhaust gas.

The FID analyzer is excellent in analysis precision, however, it is necessary to supply hydrogen gas ($H_2$) as supporting gas and helium gas (He) as carrier gas. Thus, there are problems, such as difficult handling and an increase in running costs.

Meanwhile, the FTIR analyzer has advantages of easier handling and low running costs. Patent Document 1 discloses that measurement precision is improved by previously calculating a correlation between a spectrum obtained by the FTIR analyzer and a concentration of THC indicated by the spectrum, followed by calculating a concentration of THC from the spectrum of a measurement sample by using the correlation.

PRIOR ART DOCUMENT

Patent Document

Patent Document 1: WO2019/031331

SUMMARY OF THE INVENTION

Problems to be Solved by the Invention

However, with the method disclosed in Patent Document 1 intended to calculate the THC concentration from the spectrum of the measurement object by using the correlation, the measurement precision varies due to a difference in composition of components in exhaust gas. Consequently, the THC concentration cannot be calculated precisely in some cases if a specific fuel is used or under specific combustion conditions.

In cases where exhaust gas that is a measurement sample contains only single hydrocarbon component (methane) (e.g., when engine load is small), absorbance at wavenumber absorbed only by other hydrocarbons (hydrocarbon component other than methane) which contributes to the THC concentration ought to become zero in spectrum data obtained by the FTIR device, but noise is actually present. Therefore, if the THC concentration is calculated on the basis of the obtained spectrum, noise in the absorbance at wavenumbers absorbed by other hydrocarbons are superimposely calculated, thus failing to achieve a precise calculation.

Meanwhile, if the hydrocarbon component has a high concentration, absorbance may be saturated in an obtainable spectrum. Also in this case, it is difficult to precisely calculate the THC concentration on the basis of an obtained spectrum.

Hence, a main anticipated problem of the present invention is to provide an analyzer, such as an FTIR analyzer, which achieves highly precise measurement of THC concentration in the measurement sample.

Means of Solving the Problem

In one embodiment of the present invention, an analyzer is intended to analyze a measurement sample on the basis of spectrum data obtained by irradiating light to the measurement sample. The analyzer includes a main analysis part, a correlation data storage part and a concentration calculation part. The main analysis part calculates a concentration of a predetermined hydrocarbon component contained in the measurement sample on the basis of the spectrum data of the measurement sample. The correlation data storage part stores therein a plurality of correlation data each indicating a correlation between a concentration of the predetermined hydrocarbon component or the spectrum data and a THC concentration. The concentration calculation part selects at least one correlation data from among the plurality of correlation data stored in the correlation data storage part according to the concentration of the predetermined hydrocarbon component calculated by the main analysis part, and calculates a THC concentration in the measurement sample by using one correlation data thus selected.

With the above analyzer, the plurality of correlation data each indicating a correlation between the concentration of the predetermined hydrocarbon component or the spectrum data and the THC concentration are contained in the analyzer, and the correlation data are selectable according to the concentration of the predetermined hydrocarbon component. It is therefore possible to calculate the THC concentration by using an appropriate correlation according to the composition or the like of the measurement sample. This leads to a highly precise calculation of the THC concentration even if a specific fuel is used or under specific combustion conditions.

As a specific embodiment of the analyzer, the correlation data storage part stores therein, as the plurality of correlation data, a first correlation data indicating a correlation between the concentration of the predetermined hydrocarbon component or the spectrum data and the THC concentration, and a second correlation data indicating a correlation different from the first correlation data. The concentration calculation part selects the first correlation data or the second correlation data from among the plurality of correlation data stored in the correlation data storage part according to the concentration of the predetermined hydrocarbon component calculated by the main analysis part, and calculates a THC concentration in the measurement sample by using the correlation data thus selected.

The correlation indicated by the second correlation data may be a correlation of a kind different from or identical to that of a correlation indicated by the first correlation data. For example, both the first correlation data and the second correlation data may indicate a correlation between a concentration of the predetermined hydrocarbon component and the THC concentration. Alternatively, the first correlation data may indicate a correlation between a concentration of the predetermined hydrocarbon component and the THC, and the second correlation data may indicate a correlation between the spectrum data and the THC concentration.

In a preferable embodiment of the analyzer, the first correlation data is at least one rule-based calculation model for calculating the THC concentration from the concentration of the predetermined hydrocarbon component on the basis of the correlation between the concentration of the predetermined hydrocarbon component and the THC concentration. The second correlation data is at least one machine learning model calculated by machine learning of a correlation between the spectrum data and the THC concentration. The concentration calculation part calculates the THC concentration from the spectrum data by using the at least one rule-based calculation
model or the at least one machine learning model.

With the above analyzer, a calculation of a THC concentration on the basis of the rule-based calculation model and a calculation of a THC concentration on the basis of the machine learning model obtained by previously learning correlations are selectable according to the concentration of the predetermined hydrocarbon component. Consequently, a more appropriate correlation data is selectable under various combustion conditions and used fuel conditions. This leads to a more precise calculation of the THC concentration.

If a concentration of a component other than the predetermined hydrocarbon component, for example, a concentration of a hydrocarbon component other than methane, ethylene and propylene exceeds a predetermined value, such as a lower limit level of measurement, in the analyzer, there is a possibility that a hydrocarbon component whose concentration is not yet calculated by the analyzer is contained in the measurement sample. Therefore, the THC concentration calculated from the rule-based calculation model by using the concentration of the hydrocarbon component is liable to have a large deviation from a real value.

Meanwhile, if the concentration of a component other than the predetermined hydrocarbon component does not exceed a predetermined value, such as a lower limit level of measurement in the analyzer, a calculation of a THC concentration using a previously calculated machine learning model may include large noise, failing to make a precise calculation.

For this reason, the main analysis part preferably also analyzes a concentration of a component other than the predetermined hydrocarbon component in the total hydrocarbon component. The concentration calculation part preferably calculates the THC concentration from the concentration of the predetermined hydrocarbon component by using the first correlation data (specifically, a rule based calculation model) if the concentration of the component other than the predetermined hydrocarbon component calculated by the main analysis part is a predetermined value or below. The concentration calculation part preferably calculates the THC concentration from the spectrum data by using the second correlation data (specifically, a machine learning model) if the concentration of the component other than the predetermined hydrocarbon component calculated by the main analysis part exceeds the predetermined value.

A specific embodiment of the predetermined hydrocarbon component is at least one selected from among methane ($CH_4$), ethylene ($C_2H_4$) and propylene ($C_3H_6$).

A specific embodiment of the first correlation data is a rule-based calculation model for calculating the THC concentration from the concentration of the predetermined hydrocarbon component and its weighting factor which is the number of carbon molecules contained in the predetermined hydrocarbon component.

The THC concentration calculation part preferably has a function of determining, by machine learning, one correlation data to be selected on the basis of information about correlation data selected in past, or information about one or more surrounding situations selected from among values related to physical attributes of the measurement sample, engine combustion information, engine head shape, ignition timing, catalyst composition, amount of oxygen in fuel, inorganic gas component, soot concentration, SOF concentration, engine type, engine speed, load information, hot start, cold start, oxygen concentration, catalyst temperature, and gear ratio.

In the above analyzer, the concentration calculation part preferably selects two or more from among the plurality of correlation data, calculates two or more THC concentration by using two or more correlation data thus selected, and determines a THC concentration in the measurement sample by averaging the two or more THC concentrations thus calculated.

With the above configuration, the THC concentration is calculated using a more appropriate correlation according to an analysis result obtained by the main analysis part, thus leading to further enhanced calculation precision.

A specific embodiment with which the effects of the present invention are produced remarkably, the measurement sample is automotive exhaust gas. The analyzer is preferably of so-called FTIR method using Fourier transform infrared spectroscopy.

In one embodiment of the present invention, an analysis method is intended to analyze a measurement sample on the basis of spectrum data obtained by irradiating light to the measurement sample. The analysis method includes a main analysis step, a correlation data storage step and a concentration calculation step. The main analysis step is intended to calculate a concentration of a predetermined hydrocarbon component contained in the measurement sample on the basis of the spectrum data of the measurement sample. The correlation data storage step is intended to store therein a plurality of correlation data each indicating a correlation between a concentration of the predetermined hydrocarbon component or the spectrum data and a THC concentration. The concentration calculation step is intended to select at least one correlation data from among the plurality of correlation data stored in the correlation data storage step according to the concentration of the predetermined hydrocarbon component calculated by the main analysis step, followed by calculating a THC concentration in the measurement sample by using one correlation data thus selected.

In other embodiment of the present invention, a program recording medium recorded with a program is intended for an analyzer to analyze a measurement sample on the basis of spectrum data obtained by irradiating light to the measurement sample. The program for the analyzer causes a computer to perform functions as a main analysis part, a correlation data storage part and a concentration calculation part. The main analysis part calculates a concentration of a predetermined hydrocarbon component contained in the measurement sample on the basis of the spectrum data of the measurement sample. The correlation data storage part stores therein a plurality of correlation data each indicating a correlation between a concentration of the predetermined hydrocarbon component or the spectrum data and a THC concentration. The concentration calculation part selects at least one correlation data from among the plurality of correlation data stored in the correlation data storage part according to the concentration of the predetermined hydrocarbon component calculated by the main analysis part, and calculates a THC concentration in the measurement sample by using one correlation data thus selected.

The above analysis method and the above program recording medium recorded with a program for the analyzer are capable of offering the same effects as the analyzer in the present invention described above.

Effects of the Invention

With the present invention thus configured, it is possible to provide the analyzer, such as the FTIR analyzer, which achieves highly precise measurement of the THC in the measurement sample.

DESCRIPTION OF THE EMBODIMENTS

An analyzer 100 in one of embodiments of the present invention is described below with reference to the drawings.

Figure 1:
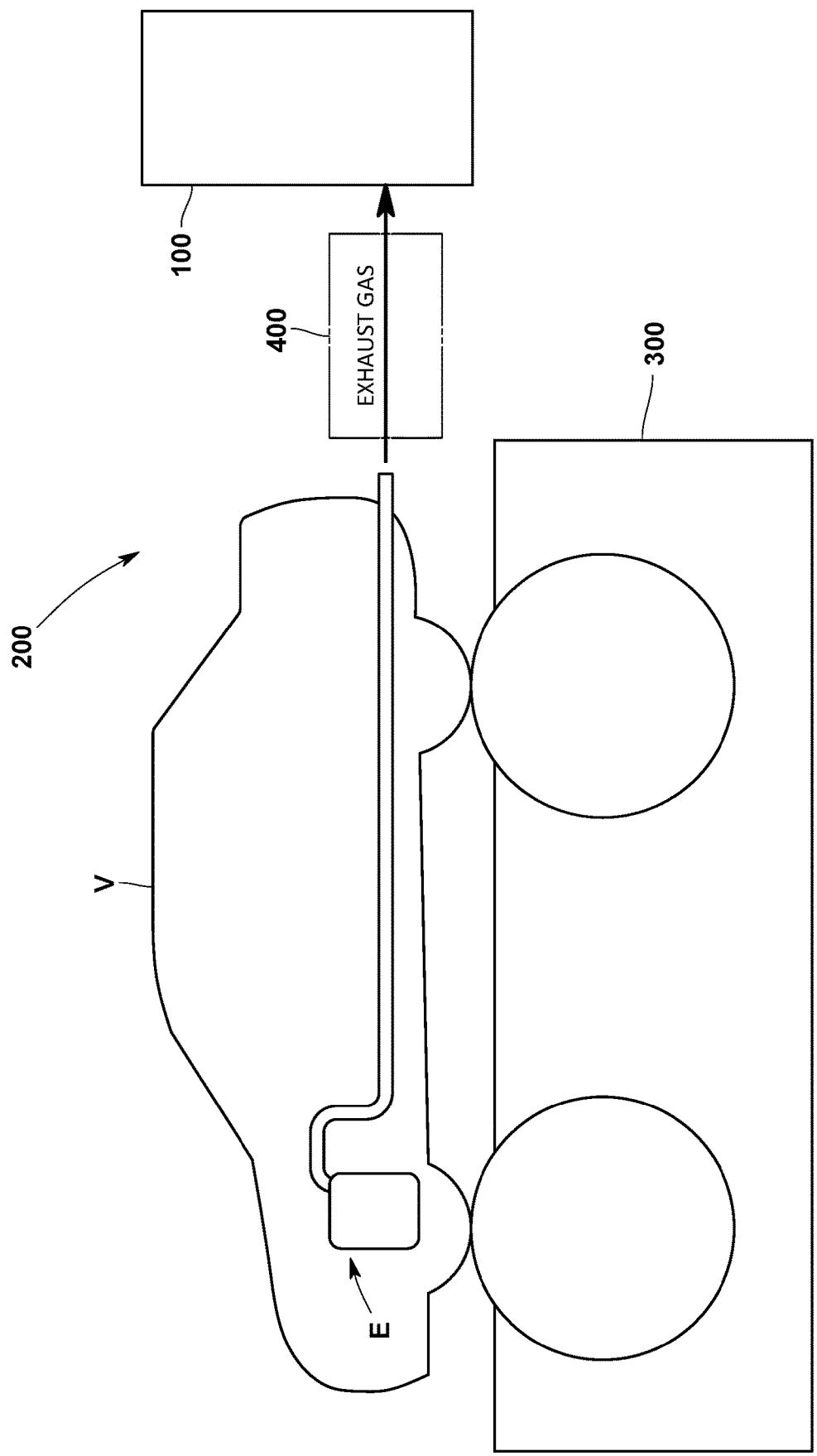
FIG. 1 is a general diagram of an exhaust gas measurement system including an analyzer in one of embodiments of the present invention.

The analyzer 100 in the present embodiment constitutes a part of, for example, an exhaust gas measurement system 200. As illustrated in FIG. 1, the exhaust gas measurement system 200 includes a chassis dynamometer 300, an exhaust gas sampling device 400 to directly sample, without diluting, exhaust gas from a test vehicle V as a specimen that runs on the chassis dynamometer 300.

Figure 2:
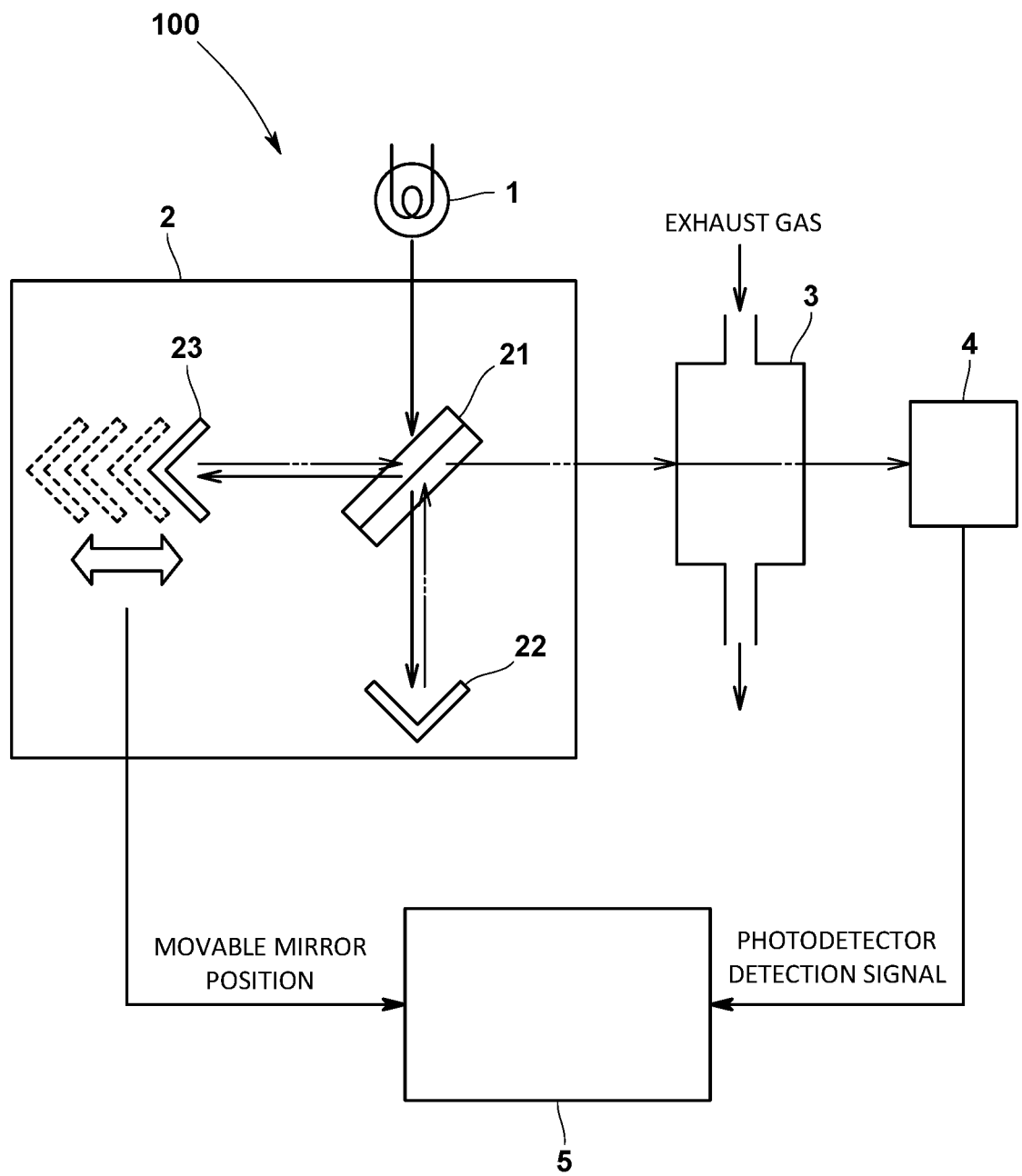
FIG. 2 is a schematic diagram illustrating the entirety of the analyzer in the embodiment.

Specifically, the analyzer 100 is an analyzer using Fourier transform infrared spectroscopy (FTIR) including, for example, an infrared light source 1, an interferometer (spectral part) 2, a measurement cell 3, a photodetector 4 and an arithmetic processing part 5 as illustrated in FIG. 2. The analyzer 100 (hereinafter also referred to as the FTIR analyzer 100 for the sake of distinction) is used as an exhaust gas analyzer to measure a concentration of total hydrocarbon (hereinafter also referred to as THC concentration) in exhaust gas as a measurement sample.

The infrared light source 1 irradiates infrared light having a broad spectrum (continuous light including lights of a large number of wavenumbers). For example, a tungsten halogen lamp or high-brightness ceramic light source is used as the infrared light source 1.

The interferometer 2 is one which uses a so-called Michelson interferometer including a half mirror (beam splitter) 21, a stationary mirror 22 and a movable mirror 23 as illustrated in FIG. 2. Infrared light from the infrared light source 1 which has entered the interferometer 2 is divided into reflected light and transmitted light by the half mirror 21. One of the lights is reflected by the stationary mirror 22, and the other is reflected by the movable mirror 23. Both return to the half mirror 21 and are combined and output from the interferometer 2.

The measurement cell 3 is a transparent cell that permits introduction of sampled exhaust gas. It is configured so that light output from the interferometer 2 passes through the exhaust gas in the measurement cell 3 into the photodetector 4.

The photodetector 4 detects infrared light after passing through the exhaust gas and outputs a detection signal (light intensity signal) thereof to the arithmetic processing part 5. The photodetector 4 is an MCT (Hg CdTe) detector in the present embodiment, but may be a photodetector including other infrared detection element.

The arithmetic processing part 5 includes, for example, an analog electric circuit including a buffer, an amplifier or the like, a digital electric circuit including a CPU, memory, DSP or the like, and an A/D converter disposed between these two circuits.

Figure 3:
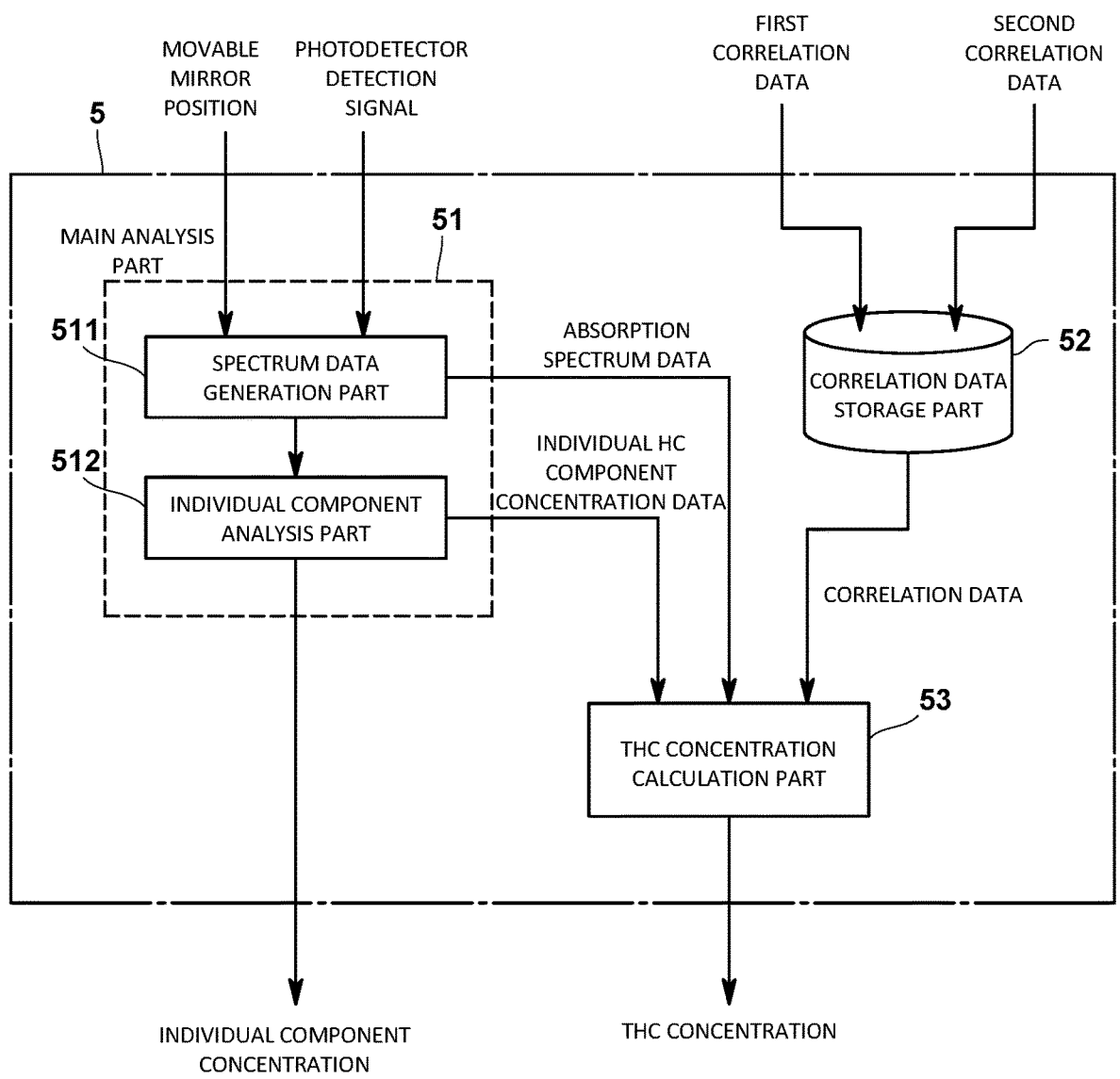
FIG. 3 is a functional block diagram of an arithmetic processing part in the embodiment.

The arithmetic processing part 5 calculates transmitted light spectrum data indicating a spectrum of the light transmitted through a sample from an output value from the photodetector 4 as illustrated in FIG. 3, by cooperation between the CPU and peripheral devices thereof according to a predetermined program stored in the memory. The arithmetic processing part 5 calculates infrared absorption spectrum data from the transmitted light spectrum data, thereby determining various components in the exhaust gas. The arithmetic processing part 5 also performs a function as a main analysis part 51 to calculate concentrations of the individual components.

The main analysis part 51 includes a spectrum data generation part 511 and an individual component analysis part 512.

If intensity of the light after passing through the exhaust gas is observed by moving forward and backward the movable mirror 23, whose position is set on a horizontal axis, light intensity draws a sine curve due to interference in the case of light of a single wave number. Actual light after passing through the exhaust gas is continuous light, and the sine curve differs depending on wave number. Therefore, actual light intensity corresponds to overlapping of sine curves drawn by individual wave numbers, and an interference pattern (interferogram) has a wave flux shape.

In the spectrum data generation part 511, the position of the movable mirror 23 is found by, for example, a range finder (not illustrated), such as a HeNe laser (not illustrated), and light intensity at individual positions of the movable mirror 23 is found by the photodetector 4. An interference pattern obtainable from these is subjected to Fast Fourier transform (FFT), thereby transforming to transmitted spectrum data whose horizontal axis is individual wave number. Then, for example, on the basis of transmitted light spectrum data obtained by previous measurement in a state in which a measurement cell is empty, the transmitted light spectrum data of the measurement sample is further transformed to absorption spectrum data.

The individual component analysis part 512 determines various components (for example, CO, $CO_2$, NO, $H_2O$, $NO_2$ and hydrocarbon component (HC)) contained in the measurement sample from, for example, individual peak positions (wave numbers) and their heights in the absorption spectrum data, and also calculates concentrations of individual components. The individual component analysis part 512 then outputs the concentrations as individual component concentration data.

As illustrated in FIG. 3, the arithmetic processing part 5 further includes functions as a correlation data storage part 52 and a THC concentration calculation part (corresponding to a concentration calculation part in the present invention)

53 in the present embodiment in order that a THC concentration of exhaust gas as a measurement sample can be measured precisely.

The correlation data storage part 52 is one which is set to a predetermined region in the memory and stores therein a plurality of correlation data each indicating a correlation between a concentration of a predetermined hydrocarbon component calculated by the individual component analysis part 512 or spectrum data generated by the spectrum data generation part 511, and a THC concentration in the measurement sample. The correlation data storage part 52 includes, as the correlation data, at least one first correlation data that is a rule-based calculation model for calculating a THC concentration from the concentration of the predetermined hydrocarbon component, and at least one second correlation data that is a machine learning model calculated by machine learning of the correlation between the spectrum data and the THC concentration. As used here, the term "predetermined hydrocarbon component" denotes methane ($CH_4$), ethylene ($C_2H_4$) and propylene ($C_3H_6$).

The rule-based calculation model indicated by the first correlation data is a calculation expression for calculating a THC concentration from the concentration of the predetermined hydrocarbon component and its weighting factor which is the number of carbon molecules contained in the predetermined hydrocarbon component. The first correlation data may be previously stored in the correlation data storage part 52, or alternatively may be inputted suitably by a user. A specific example of the calculation expression is as indicated in the following equation (1).

$$[THC]=a_1 \cdot [CH_4]+a_2 \cdot [C_2H_4]+a_3 \cdot [C_3H_6]+ \ldots \quad (1)$$

As used here, the term [THC] denotes a THC concentration, $[CH_4]$, $[C_2H_4]$, $[C_3H_6]$ and the like are concentrations of individual hydrocarbon components, and $a_1$, $a_2$, $a_3$ . . . are weighting factors.

The correlation data storage part 52 stores therein a plurality of first correlation data different in rule-based calculation model in order that the THC concentration can be obtained more precisely according to the concentration of individual hydrocarbon components in the measurement sample. The correlation data storage part 52 stores, as the first correlation data, $CH_4$-THC correlation data, $CH_4 \cdot C_2H_4$-THC correlation data, $CH_4 \cdot C_2H_4 \cdot C_3H_6$-THC correlation data and the like. Operation models respectively indicated by the first correlation data are as indicated in the following expressions (2) to (4).

$$[THC]=[CH_4] \quad (2)$$

$$[THC]=[CH_4]+2 \cdot [C_2H_4] \quad (3)$$

$$[THC]=[CH_4]+2 \cdot [C_2H_4]+3 \cdot [C_3H_6]. \quad (4)$$

The machine learning model indicated by the second correlation data is one which is previously calculated by a machine learning device disposed separately from the analyzer 100, and stored in the correlation data storage part 52 as learned data.

Specifically, the machine learning model is calculated by analyzing and learning a reference sample (exhaust gas) in the machine learning device by using the FID analyzer and the FTIR analyzer.

More specifically, a THC concentration of the reference sample (exhaust gas) is measured using the FID analyzer, and the reference sample is also introduced into the FTIR analyzer so as to obtain absorption spectrum data thereof. The measured THC concentration and the obtained absorption spectrum data are linked into reference sample data. The machine learning model is obtainable by preparing a plurality of the reference sample data and by calculating, through machine learning, a correlation between the absorption spectrum data and the THC concentration.

The THC concentration calculation part 53 calculates a THC concentration in the measurement sample on the basis of an analysis result obtained by the main analysis part 51. More specifically, the THC concentration calculation part 53 obtains absorption spectrum data and individual component concentration data (specifically, individual HC component concentration data indicating concentrations of individual hydrocarbon component) from the main analysis part 51, and correlation data from the correlation data storage part 52, and then calculates the THC concentration in the measurement sample on the basis of these data.

Thus, the THC concentration calculation part 53 in the present embodiment selects at least one correlation data from the correlation data storage part 52 according to a concentration of hydrocarbon component calculated by the main analysis part 51, and calculates the THC concentration in the measurement sample by using the correlation data thus selected. In the present embodiment, the THC concentration calculation part 53 selects the first correlation data or the second correlation data according to the concentration of hydrocarbon component calculated by the main analysis part 51, and the calculates the THC concentration in the measurement sample by using the selected data.

Specifically, the THC concentration calculation part 53 in the present embodiment selects the first correlation data if a concentration of a hydrocarbon component of any one of methane, ethylene and propylene in concentrations of individual hydrocarbon components calculated by the main analysis part 51 exceeds a predetermined value (specifically, a lower limit of measurement, namely, a noise level), and if all the concentrations of hydrocarbon components other than methane, ethylene and propylene are the predetermined value (specifically, the lower limit of measurement, namely, the noise level) or below. Then, the THC concentration calculation part 53 calculates the THC concentration in the measurement sample by applying the concentrations of the individual hydrocarbon components calculated by the main analysis part 51 to the operation model indicated by the selected first correlation data.

In this case, the THC concentration calculation part 53 selects a proper single first correlation data according to the concentrations of methane, ethylene and propylene (predetermined hydrocarbon components), and calculates the THC concentration in the measurement sample by using the selected first correlation data.

Specifically, if the concentration of methane calculated by the main analysis part 51 exceeds the noise level and does not exceed an upper limit level of calibration curve, and if all the concentrations of hydrocarbon components other than methane are the noise level or below, the THC concentration calculation part 53 selects $CH_4$-THC correlation data that indicates the operation model indicating a correlation between a methane concentration and a THC concentration. Then, the THC concentration calculation part 53 calculates a THC concentration in the measurement sample by assigning the methane concentration, which is calculated by the individual component analysis part 512 on the basis of absorption spectrum data, to the following equation (5).

$$[THC]_{(M)}=[CH_4]_{(M)} \quad (5)$$

As used here, $[THC]_{(M)}$ is a THC concentration of a measurement sample calculated by the THC concentration calculation part 53, and $[CH_4]_{(M)}$ is a methane concentration in the measurement sample calculated by the individual component analysis part 512.

Meanwhile, if the concentration of methane and ethylene calculated by the main analysis part 51 exceeds the noise level and does not exceed an upper limit level of calibration curve, and if all the concentrations of hydrocarbon components other than methane and ethylene are the noise level or below, the THC concentration calculation part 53 selects $CH_4.C_2H_4$-THC correlation data that indicates the operation model indicating a correlation between concentrations of methane and ethylene and a THC concentration. Then, the THC concentration calculation part 53 calculates a THC concentration in the measurement sample by assigning the concentrations of methane and ethylene, which are calculated by the individual component analysis part 512 on the basis of the absorption spectrum data, to the following equation (6).

$$[THC]_{(M)}=[CH_4]_{(M)}+2.[C_2H_4]_{(M)} \quad (6)$$

As used here, $[C_2H_4]_{(M)}$ is an ethylene concentration in a measurement sample calculated by the individual component analysis part 512.

Meanwhile, if the concentration of methane, ethylene and propylene calculated by the main analysis part 51 exceeds the noise level and does not exceed the upper limit level of calibration curve, and if all the concentrations of hydrocarbon components other than methane, ethylene and propylene does not exceed the noise level, the THC concentration calculation part 53 selects $CH_4.C_2H_4.C_3H_6$-THC correlation data that indicates the operation model indicating a correlation between concentrations of methane, ethylene and propylene and a THC concentration. Then, the THC concentration calculation part 53 calculates a THC concentration in the measurement sample by assigning the concentrations of methane, ethylene and propylene, which are calculated by the individual component analysis part 512 on the basis of the absorption spectrum data, to the following equation (7).

$$[THC]_{(M)}=[CH_4]_{(M)}+2.[C_2H_4]_{(M)}+3.[C_3H_6]_{(M)} \quad (7)$$

As used here, $[C_3H_6]_{(M)}$ is a propylene concentration in a measurement sample calculated by the individual component analysis part 512.

Meanwhile, if any one of the concentrations of methane, ethylene or propylene calculated by the main analysis part 51 exceeds a predetermined value (the noise level), and if a concentration of a hydrocarbon component other than methane, ethylene and propylene exceeds a predetermined value (the noise level), the THC concentration calculation part 53 selects the second correlation data. Then, the THC concentration calculation part 53 calculates a THC concentration in the measurement sample by applying absorption spectrum data obtained from the spectrum data generation part to a machine learning model indicated by the second correlation data. In this case, the THC concentration calculation part 53 selects an appropriate single second correlation data according to the concentrations of methane, ethylene and propylene (a predetermined hydrocarbon component), and calculates a THC concentration in the measurement sample by using the selected second correlation data.

The THC concentration calculation part 53 may select either one of the first correlation data and the second correlation data if all the concentrations of methane, ethylene and propylene calculated by the main analysis part 51 are the predetermined value (noise level) or below, and if the concentrations of all hydrocarbon components other than methane, ethylene and propylene are the predetermined value (noise level) or below.

Effects of Present Embodiment

With the analyzer 100 thus configured, the plurality of correlation data each indicating the correlation between the predetermined hydrocarbon component concentrations or the spectrum data and the THC concentration are contained therein, and the correlation data are selectable according to the hydrocarbon component concentration calculated by the main analysis part 51. It is therefore possible to calculate the THC concentration by using an appropriate correlation according to the composition or the like of the measurement sample. This leads to a highly precise calculation of the THC concentration even if a specific fuel is used or under specific combustion conditions.

Other Modified Embodiments

The present invention is not limited to the above embodiments.

Although the predetermined hydrocarbon components are three components of methane, ethylene and propylene in the above embodiments, there is no intention to limit thereto. The predetermined hydrocarbon components may be one or more arbitrary components selected from among methane, ethylene and propylene in other embodiments.

In the above embodiment, if the concentrations of hydrocarbon components other than methane, ethylene and propylene among the concentrations of individual hydrocarbon components calculated by the main analysis part 51 are the noise level or below, the THC concentration calculation part 53 selects the rule-based calculation model (namely, the first correlation data). If the concentration of any one of hydrocarbon components other than methane, ethylene and propylene exceeds the noise level or below, the THC concentration calculation part 53 selects the machine learning model (namely, the second correlation data). However, there is no intention to limit thereto.

In an alternative embodiment, also, if any one of the concentrations of individual hydrocarbon components other than methane, ethylene and propylene calculated by the main analysis part 51 exceeds the noise level, the THC concentration calculation part 53 may select the rule-based calculation model (namely, the first correlation data), and may calculate a THC concentration of a measurement sample on the basis of the rule-based calculation model.

In other alternative embodiment, if all the concentrations of methane, ethylene and propylene calculated by the main analysis part 51 exceed the noise level and an upper limit level of calibration curve, and if all concentrations of other hydrocarbon components are the noise level or below, the THC concentration calculation part 53 may select the machine learning model (the second correlation data), and may calculate a THC concentration of a measurement sample on the basis of the machine learning model.

In still other embodiment, if any one of the concentrations of methane, ethylene and propylene calculated by the main analysis part 51 exceeds the upper limit level of calibration curve, the THC concentration calculation part 53 may select the machine learning model and calculate a THC concentration in a measurement sample by applying the spectrum data to the machine learning model.

For obtaining a more accurate THC concentration, the correlation data storage part 52 may store therein a plurality of different machine learning models (second correlation data) each indicating a direct correlation between spectrum data and THC concentration. These machine learning models may be created separately according to various parameter magnitudes, such as individual hydrocarbon component concentrations, THC concentration, and areas and shapes of the spectrum data.

If the correlation data storage part 52 stores therein a plurality of machine learning models (second correlation data), the THC concentration calculation part 53 may be configured to select optimum second correlation data from among the plurality of second correlation data stored in the correlation data storage part 52 by machine learning upon receipt of an analysis result obtained by the main analysis part 51 (spectrum data and individual component concentration data). Specifically, in terms of the plurality of stored different machine learning models (second correlation data), the THC concentration calculation part 53 may be configured to find regularity (clustering) by machine learning on the basis of individual HC component concentrations and spectrum data characteristics. For example, the regularity may be found out by k-means and other method. Upon receipt of the spectrum data and individual component concentration data from the main analysis part 51, the second correlation data indicating an optimum machine learning model may be selected on the basis of the found regularity. Alternatively, the THC concentration calculation part 53 may be configured to select an optimum second correlation data from among the plurality of second correlation data stored in the correlation data storage part 52 on the basis of a predetermined algorithm.

If the correlation data storage part 52 stores therein one or a plurality of first correlation data and one or a plurality of second correlation data, the THC concentration calculation part 53 may be configured to determine, by machine learning, correlation data to be selected. In this case, the THC concentration calculation part 53 may be configured to select an optimum correlation data by learning information about analysis situations related to analysis conditions (for example, information about selected correlation data, information about a calculated THC concentration value calculated using the selected correlation data, and information about noise magnitude) in a plurality of past analyses (specifically, latest one or a plurality of analyses), and information about surrounding situations related to measurement conditions or the like described later. Alternatively, the THC concentration calculation part 53 may be configured to select an optimum correlation data from one or a plurality of first correlation data and second correlation data on the basis of a predetermined algorithm.

If there are a plurality of correlation data serving as a selection candidate, the THC concentration calculation part 53 may select two or more from among the plurality of correlation data, and may calculate a THC concentration on the basis of the selected two or more correlation data. For example, a new correlation may be calculated by averaging correlations individually indicated by a plurality of different correlation data with the use of various techniques, such as arithmetic mean and weighted average, and a THC concentration may be calculated on the basis of the calculated correlation. Alternatively, a new correlation may be calculated by machine learning from correlations indicated by a plurality of selected correlation data. Still alternatively, a plurality of THC concentrations may be calculated on the basis of correlations individually indicated by the plurality of selected correlation data, and a THC concentration in a measurement sample may be calculated by averaging a plurality of calculated THC concentrations. In the case of selecting a plurality of correlation data, only a plurality of first correlation data may be selected, only a plurality of second correlation data may be selected, or at least one first correlation data and at least one second correlation data may be selected.

A correlation expressed by the machine learning model indicated by the second correlation data may employ, as a parameter, information about the surrounding situations, such as measurement conditions. Examples of the surrounding situations include values related to physical attributes, such as temperature and pressure of a measurement sample, combustion information about an engine (information related to supercharging, EGR, rich/stoichiometric/lean, laminar flow, uniform flow, direct injection, and port injection), engine head shape, ignition timing, catalyst composition, amount of oxygen in fuel, inorganic gas component, soot concentration, SOF concentration, engine type, engine speed, load information, hot start, cold start, oxygen concentration, catalyst temperature, and gear ratio. A correlation expressed by the machine learning model may employ, as a parameter, a part or all of these surrounding situations. Alternatively, only surrounding situations that strongly affect (are highly related to) a THC concentration calculated by the analyzer 100 may be employed as a parameter.

Figure 4:
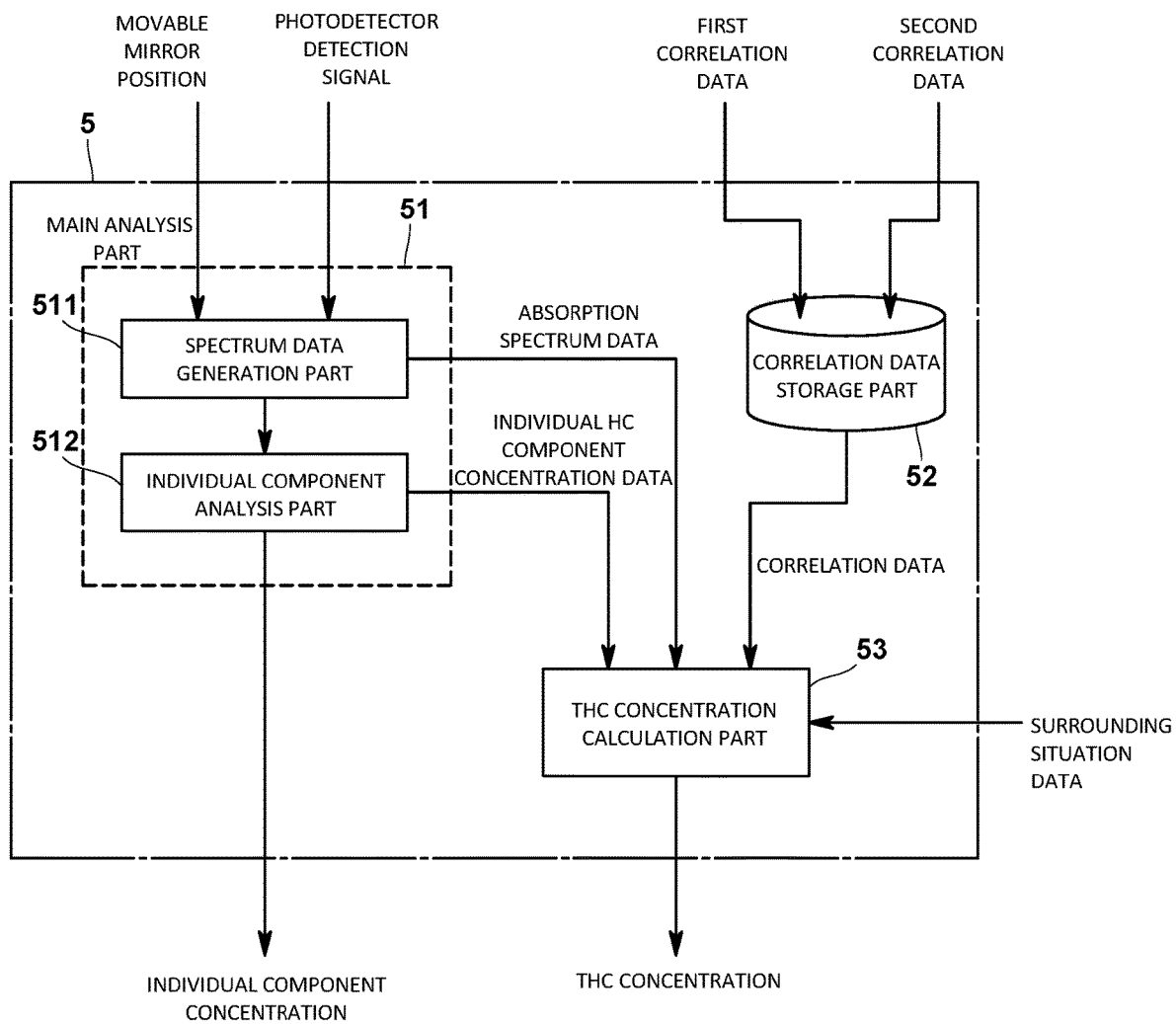
FIG. 4 is a functional block diagram of an arithmetic processing part in other embodiment.

Thus, if the correlation expressed by the machine learning model employs the surrounding situations as a parameter, the THC concentration calculation part 53 may be configured to acquire surrounding situation data through an input by a sensor or an operator as illustrated in FIG. 4. Then, the THC concentration calculation part 53 may calculate a THC concentration by applying the spectrum data and the surrounding situation data to the machine learning model. With the above configuration, the surrounding situation data highly related to the THC concentration, namely, a design parameter, can be grasped, making it possible to provide the design parameter as a design development support system for an automobile manufacturer or a catalyst manufacturer.

The exhaust measurement system in the present embodiment is intended to test a completed vehicle V by using the chassis dynamometer 300. Alternatively, the system may be intended to test engine performance by using, for example, an engine dynamometer, or test power train performance by using the dynamometer.

The analyzer 100 may be configured to irradiate light to a measurement sample so as to make an analysis from a spectrum thereof. The analyzer 100 is also applicable to NDIR and ones other than spectroscopic analyzers, such as light scattering particle size distribution measuring device. The present invention is not limited to an automotive exhaust gas analysis, but is also capable of analyzing exhaust gas of internal combustion engines of, for example, ships, aircrafts, agricultural machinery and machine tools.

Besides the above embodiments, various modifications can be made without departing from the spirit and scope of the present invention.

DESCRIPTION OF THE REFERENCE NUMERAL

100 analyzer
51 main analysis part
52 correlation data storage part
53 THC concentration calculation part (concentration calculation part)

What is claimed is:

1. An analyzer to analyze a measurement sample on a basis of spectrum data obtained by irradiating light to the measurement sample, comprising:
one or more computers programmed to
calculate a concentration of a predetermined hydrocarbon component contained in the measurement sample on the basis of the spectrum data of the measurement sample;
store first and second correlation data, wherein the first correlation data is at least one model for calculating a THC concentration that is based on a correlation between the concentration of the predetermined hydrocarbon component or the spectrum data and the THC concentration, and wherein the second correlation data is at least one model for calculating the THC concentration that is based on the correlation between the concentration of the predetermined hydrocarbon component or the spectrum data and the THC concentration;
select at least one of the first and second correlation data according to the calculated concentration of the predetermined hydrocarbon component; and
calculate a THC concentration in the measurement sample by using the selected at least one of the first and second correlation data.

2. The analyzer according to claim 1, wherein
the first correlation data is at least one rule-based calculation model for calculating the THC concentration, and
the second correlation data is at least one machine learning model calculated by machine learning for calculating the THC concentration.

3. The analyzer according to claim 2, wherein the one or more computers are further programmed to
analyze a concentration of a component other than the predetermined hydrocarbon component in the THC concentration,
calculate the THC concentration from the concentration of the predetermined hydrocarbon component by using the first correlation data responsive to the concentration of the component other than the predetermined hydrocarbon component being a predetermined value or below, and
calculate the THC concentration from the spectrum data by using the second correlation data responsive to the concentration of the component other than the predetermined hydrocarbon component exceeding the predetermined value.

4. The analyzer according to claim 1, wherein the predetermined hydrocarbon component is at least one selected from among methane ($CH_4$), ethylene ($C_2H_4$), and propylene ($C_3H_6$).

5. The analyzer according to claim 1, wherein the first correlation data is a rule-based calculation operation model for calculating the THC concentration from the concentration of the predetermined hydrocarbon component and a weighting factor, which is a number of carbon molecules contained in the predetermined hydrocarbon component.

6. The analyzer according to claim 1, wherein the one or more computers are further programmed to select, by machine learning, one correlation data on a basis of information about correlation data selected in past, or information about one or more surrounding situations selected from among values related to physical attributes of the measurement sample, engine combustion information, engine head shape, ignition timing, catalyst composition, amount of oxygen in fuel, inorganic gas component, soot concentration, SOF concentration, engine type, engine speed, load information, hot start, cold start, oxygen concentration, catalyst temperature, and gear ratio.

7. The analyzer according to claim 1, wherein the one or more computers are further programmed to select two or more from among the plurality of correlation data, calculate two or more THC concentrations by using the selected two or more correlation data, and determine a THC concentration in the measurement sample by averaging the calculated two or more THC calculations.

8. The analyzer according to claim 1, wherein the measurement sample is automotive exhaust gas.

9. The analyzer according to claim 1, using Fourier transform infrared spectroscopy.

10. An analysis method for analyzing a measurement sample on a basis of spectrum data obtained by irradiating light to the measurement sample, the analysis method comprising:
calculating a concentration of a predetermined hydrocarbon component contained in the measurement sample on the basis of the spectrum data of the measurement sample;
storing first and second correlation data, wherein the first correlation data is at least one model for calculating a THC concentration that is based on a correlation between the concentration of the predetermined hydrocarbon component or the spectrum data and the THC concentration, and wherein the second correlation data is at least one model for calculating the THC concentration that is based on the correlation between the concentration of the predetermined hydrocarbon component or the spectrum data and the THC concentration;
selecting at least one of the first and second correlation data according to the calculated concentration of the predetermined hydrocarbon component; and
calculating a THC concentration in the measurement sample by using the selected at least one of the first and second correlation data.

11. An analyzer to analyze a measurement sample on a basis of spectrum data obtained by irradiating light to the measurement sample, comprising:
one or more computers programmed to
calculate a concentration of a predetermined hydrocarbon component contained in the measurement sample on the basis of the spectrum data of the measurement sample,
store a first correlation data indicating a correlation between the concentration of the predetermined hydrocarbon component or the spectrum data and a THC concentration, and a second correlation data indicating a correlation different from the first correlation data, wherein the first correlation data is at least one rule-based calculation model for calculating the THC concentration from the concentration of the predetermined hydrocarbon component on a basis of a correlation between the concentration of the predetermined hydrocarbon component and the THC concentration and the second correlation data is at least one machine learning model calculated by machine learning of a correlation between the spectrum data and the THC concentration,
select the first correlation data or the second correlation data according to the calculated concentration of the predetermined hydrocarbon component, and calculate the THC concentration in the measurement sample by using the at least one rule-based calculation model or the at least one machine learning model.

12. An analyzer to analyze a measurement sample on a basis of spectrum data obtained by irradiating light to the measurement sample, comprising:

one or more computers programmed to calculate a concentration of a predetermined hydrocarbon component contained in the measurement sample on the basis of the spectrum data of the measurement sample, wherein the predetermined hydrocarbon component is at least one selected from among methane ($CH_4$), ethylene ($C_2H_4$), and propylene ($C_3H_6$);

store a plurality of correlation data each indicating a correlation between a concentration of the predetermined hydrocarbon component or the spectrum data and a THC concentration;

select at least one correlation data from among the plurality of stored correlation data according to the calculated concentration of the predetermined hydrocarbon component; and calculate a THC concentration in the measurement sample by using the selected correlation data.

* * * * *